US00PP27848P3

(12) United States Plant Patent
Bergman

(10) Patent No.: US PP27,848 P3
(45) Date of Patent: Apr. 4, 2017

(54) ***CHRYSANTHEMUM* PLANT NAMED 'CIDZ0067'**

(50) Latin Name: *Chrysanthemum×morifolium*
Varietal Denomination: CIDZ0067

(71) Applicant: SYNGENTA PARTICIPATIONS AG, Basel (CH)

(72) Inventor: Wendy R. Bergman, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 95 days.

(21) Appl. No.: 14/756,150

(22) Filed: Aug. 7, 2015

(65) Prior Publication Data

US 2016/0057908 P1 Feb. 25, 2016

Related U.S. Application Data

(60) Provisional application No. 62/039,706, filed on Aug. 20, 2014.

(51) Int. Cl.
*A01H 5/02* (2006.01)

(52) U.S. Cl.
USPC ..... Plt./287

(58) Field of Classification Search
USPC ..... Plt./287
See application file for complete search history.

(56) References Cited

PUBLICATIONS

UPOV hit on *Chrysanthemum* 'CIDZ0067', CA PBR 13-8106, published Oct. 31, 2013.*

* cited by examiner

*Primary Examiner* — Anne Grunberg
(74) *Attorney, Agent, or Firm* — Dale Skalla

(57) ABSTRACT

A new *Chrysanthemum* plant named 'CIDZ0067' particularly distinguished by the green colored, decorative-type inflorescences, dark green, glossy foliage, excellent strength and uniformity of plant habit, and a flowering response of 8 weeks under short day conditions.

1 Drawing Sheet

Latin name of the genus and species of the plant claimed: *Chrysanthemum×morifolium.*

Varietal denomination: 'CIDZ0067'.

BACKGROUND OF THE NEW PLANT

The present invention comprises a new *Chrysanthemum*, botanically known as *Chrysanthemum×morifolium*, and hereinafter referred to by the variety name 'CIDZ0067'.

'CIDZ0067' is a product of a planned breeding program. The new cultivar has green colored, decorative-type inflorescences, dark green, glossy foliage, excellent strength and uniformity of plant habit, and a flowering response of 8 weeks under short day conditions.

'CIDZ0067' originated from a hybridization made in February 2008 in a greenhouse in Bogota, Colombia. The female parent was the unpatented, proprietary plant designated 'A8327', having white decorative-type flowers with a green center, and larger flower size than with flowers of 'CIDZ0067'.

The male parent of 'CIDZ0067' was the unpatented, proprietary plant designated as 'B2493', with white and green decorative-type inflorescences that are somewhat smaller in size and develop more disk florets when compared with flowers of 'CIDZ0067'.

The resultant seed was sown in March 2011 and grown in Gilroy, Calif. 'CIDZ0067' was selected as a single flowering plant within the progeny of the stated cross in August 2011 in Gilroy, Calif.

The first act of asexual reproduction of 'CIDZ0067' was accomplished when vegetative cuttings were propagated from the initial selection in November 2011 in a greenhouse in Gilroy, Calif.

BRIEF SUMMARY OF INVENTION

Horticultural examination of plants grown from cuttings of the plant initiated in April 2012, and continuing thereafter, has demonstrated that the combination of characteristics as herein disclosed for 'CIDZ0067' are firmly fixed and are retained through successive generations of asexual reproduction.

'CIDZ0067' has not been observed under all possible environmental conditions. The phenotype may vary significantly with variations in environment such as temperature, light intensity, and day length.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0067' with colors being as true as possible with an illustration of this type.

Figure 1:
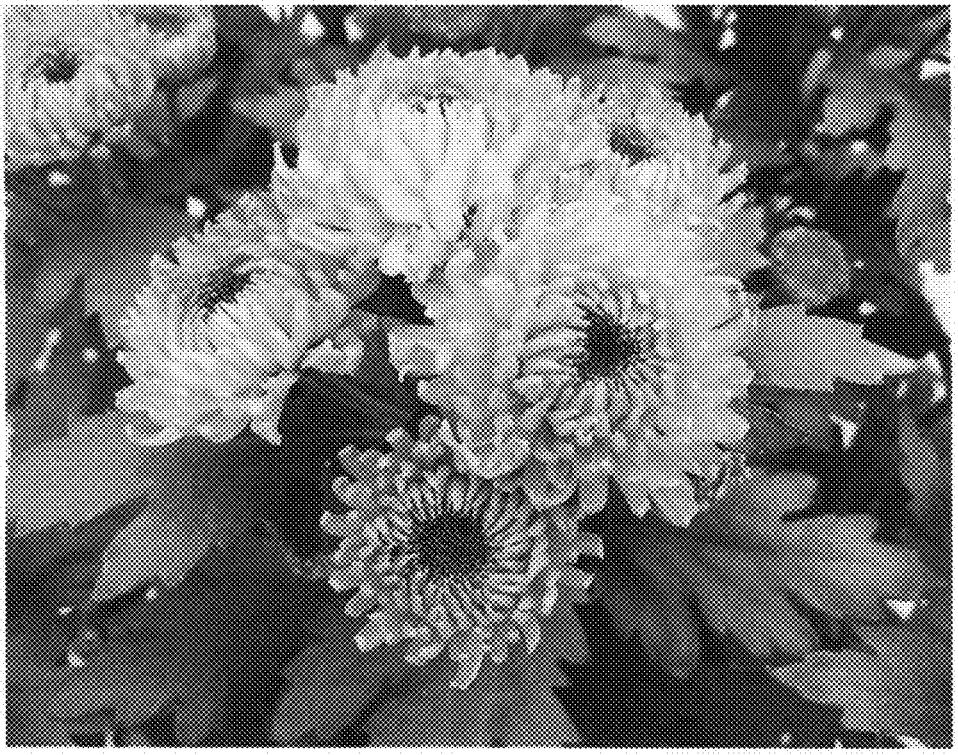
Figure 2:
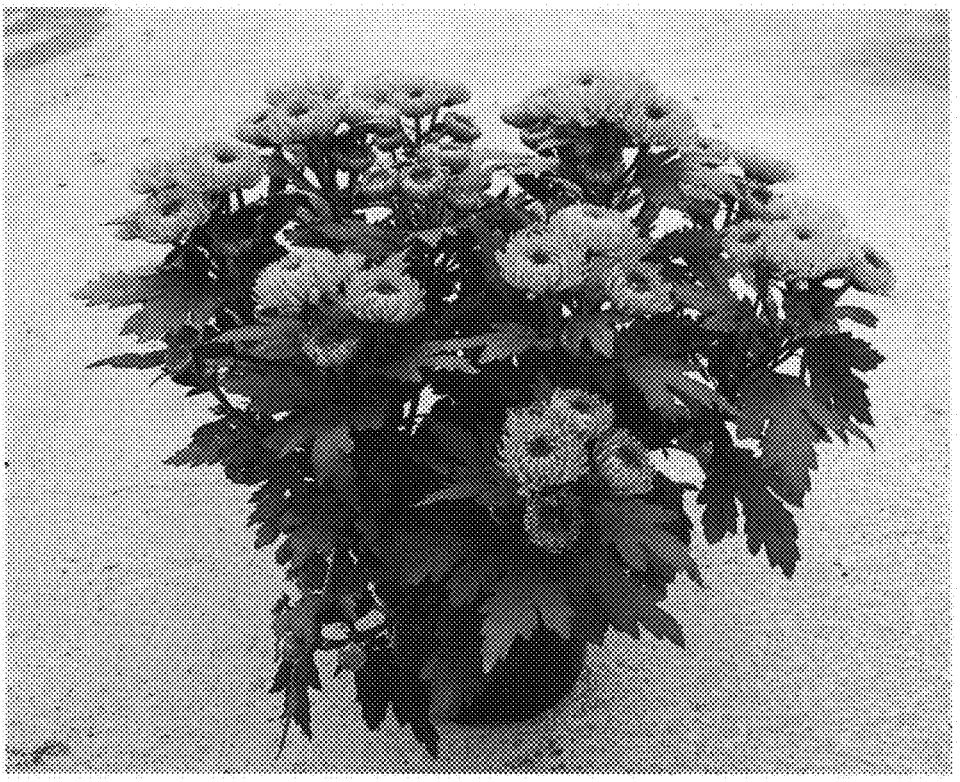

The photographic drawings show in FIG. 1 a close-up of a inflorescence of the new variety and in FIG. 2 a whole flowering plant.

DETAILED BOTANICAL DESCRIPTION

The plant descriptions and measurements were taken indoors in Nipomo, Calif. in August 2014 on about 11 week old plants. Unrooted cuttings had been planted, 4 plants per pot, in 6 inch pots on May 24, 2014. The plants were pinched and moved to short days on Jun. 16, 2014 to induce flowering.

The aforementioned photographs, FIGS. 1 and 2 were taken in Gilroy, Calif. in March 2012, and showing a plant from a trial, in which flowering had been induced by applying black cloth. These plants were about 11 weeks of age. Unrooted cuttings had been planted, 4 plants per pot, in 6 inch pots in January 2012. The plants were pinched and moved to short days to induce flowering.

Color references are made to The Royal Horticultural Society Colour Chart (R.H.S.) 2001.

TABLE 1

DIFFERENCES BETWEEN THE NEW VARIETY 'CIDZ0067' AND A MOST SIMILAR VARIETY

| | 'CIDZ0067' | 'YOGREEN VALLEY', U.S. Pat. No. PP19,629 |
|---|---|---|
| All over color of the inflorescence: | Greener | More green-yellow |
| Flower shape: | Decorative type with very few or no disc florets | A few more disc florets |
| Foliage color: | Darker green, more glossy | Less deep green, duller leaves |
| Foliage, resistance to leaf miner: | Better | More susceptible |

Plant:

*Form, growth and habit.*—Herbaceous pot-type, stems upright, freely branching, strong and moderately vigorous growth habit.

*Plant height.*—22.0-25.0 cm.

*Plant height (inflorescence included).*—27.0-30.0 cm.

*Plant width.*—27.0-30.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—RHS 137B.

*Lower surface.*—RHS 147B.

*Mature, leaf color, upper surface.*—Closest to RHS 137A.

*Lower surface.*—RHS 147B.

*Length.*—7.0-8.0 cm.

*Width.*—5.0-6.0 cm.

*Shape.*—Ovate.

*Base shape.*—Attenuate.

*Apex shape.*—Mucronulate.

*Margin.*—Palmately lobed; irregularly incised, somewhat serrate.

*Texture, upper surface.*—Bifid T-shaped hairs.

*Lower surface.*—Bifid T-shaped hairs.

*Color of veins, upper surface.*—RHS 147D.

*Color of veins, lower surface.*—RHS 147B.

*Pattern of veining.*—Palmate.

*Petiole color.*—RHS 137A.

*Length.*—1.0-1.8 cm.

*Diameter.*—0.3-0.5 cm.

*Texture.*—Bifid T-shaped hairs.

Stem:

*Quantity of main branches per plant.*—3-4.

*Color of stem.*—RHS 146A.

*Length of stem.*—17.0-20.0 cm.

*Diameter.*—0.4-0.5 cm.

*Length of internodes.*—0.7-2.8 cm.

*Texture.*—Bifid T-shaped hairs.

*Color of peduncle.*—RHS 146A.

*Length of peduncle.*—2.5-5.0 cm.

*Peduncle diameter.*—0.2 cm.

*Texture.*—Bifid T-shaped hairs.

Inflorescence:

*Type.*—Compositae type, solitary decorative-type inflorescences borne terminally above foliage, ray florets arranged acropetally on a capitulum.

*Quantity of short days to flowering (response time).*—8 weeks.

*Natural season flowering.*—Not determined on this variety.

*Quantity of inflorescences per plant.*—65-80.

*Lastingness of individual blooms on the plant.*—4 weeks.

*Fragrance.*—Slightly spicy.

Bud (just when opening/showing color):

*Color.*—Closest to RHS 144C.

*Length.*—0.8-1.0 cm.

*Width.*—1.3 cm.

*Shape.*—Oblate.

Immature inflorescence:

*Diameter.*—4.0-5.0 cm.

*Color of ray florets, upper surface.*—Closest to RHS 144B.

*Lower surface.*—Closest to RHS 144C.

Mature inflorescence:

*Diameter.*—5.0-6.0 cm.

*Depth.*—2.0-2.5 cm.

*Total diameter of disc.*—None.

*Receptacle color.*—RHS 145B.

*Receptacle height.*—0.5-0.6 cm.

*Receptacle diameter.*—0.8-0.9 cm.

Ray florets:

*Average quantity of florets.*—270.

*Color of florets, upper surface.*—Closest to RHS 145D and 144B.

*Lower surface.*—Closest to RHS 145C and 144B.

*Length.*—3.2-3.7 cm.

*Width.*—0.45-0.6 cm.

*Shape.*—Incurved.

*Apex shape.*—Acute and retuse.

*Margin.*—Entire.

*Texture, upper surface.*—Papillose.

*Lower surface.*—Papillose.

Disc florets:

*Average quantity of florets.*—0-5.

*Color of florets.*—RHS 7B basally fading to more RHS 155D with a RHS 7B apex.

*Length.*—1.0-1.6 cm.

*Width.*—0.15-0.3 cm when open.

*Shape.*—Tubular, elongated.

*Apex shape.*—Acute, 5 pointed.

Phyllaries:

*Quantity*.—About 25.
*Color, upper surface*.—Lighter than RHS 138D.
*Lower surface*.—RHS 138B.
*Length*.—0.5-0.8 cm.
*Width*.—0.15-0.2 cm.
*Shape*.—Lanceolate.
*Apex shape*.—Acute.
*Base*.—Fused.
*Margins*.—Entire; slightly papery.
*Texture, upper surface*.—Glabrous.
*Lower surface*.—Bifid T-shaped hairs.

Reproductive organs:

*Pistil*.—1, found on both types of florets.
*Length*.—0.6 cm.
*Style color*.—RHS 155C.
*Style length*.—0.45 cm.
*Stigma color*.—RHS 17C.
*Stigma shape*.—Bi-parted.
*Ovary color*.—RHS 155C but more translucent.
*Stamens*.—4, found on only on the disc florets.
*Color of filaments*.—RHS 155C.
*Length filaments*.—0.4-0.5 cm.
*Anther color*.—RHS 15A.
*Anther length*.—0.15 cm.
*Anther shape*.—Oval.
*Color of pollen*.—RHS 17B.
*Pollen amount*.—Sparse.
*Fertility/seed set*.—Has not been observed to date.
*Disease/pest resistance*.—Has not been observed to date.

What is claimed is:

1. A new and distinct variety of *Chrysanthemum* plant named 'CIDZ0067' substantially as and described herein.

* * * * *